United States Patent [19]

Menard

[11] Patent Number: 5,755,710
[45] Date of Patent: May 26, 1998

[54] ABSORBENT ARTICLE HAVING STRIKE WINDOW

[75] Inventor: Michael Joseph Menard, Doylestown, Pa.

[73] Assignee: McNeil-PPC, Inc., Skillman, N.J.

[21] Appl. No.: 460,333

[22] Filed: Jun. 2, 1995

Related U.S. Application Data

[62] Division of Ser. No. 767,294, Sep. 27, 1991, abandoned.

[51] Int. Cl.$^6$ ........................................... A61F 13/15
[52] U.S. Cl. ........................................ 604/378; 604/385.1
[58] Field of Search ........................... 604/358, 370, 604/378, 383, 385.1

[56] References Cited

U.S. PATENT DOCUMENTS

| | | | |
|---|---|---|---|
| 1,946,626 | 2/1934 | Jurgensen | 604/358 |
| 2,896,627 | 7/1959 | Harwood | 604/370 |
| 3,520,303 | 7/1970 | Endres | 604/370 |
| 3,888,254 | 6/1975 | Hendricks | 604/370 |
| 4,333,465 | 6/1982 | Wiegner | 604/385.1 |
| 5,176,672 | 1/1993 | Bruemmer et al. | 604/385.1 |
| 5,188,626 | 2/1993 | Toyoda et al. | 604/385.1 |
| 5,415,640 | 5/1995 | Kirby et al. | 604/383 |
| 5,496,626 | 3/1996 | Hamajima et al. | 604/358 |
| 5,533,991 | 7/1996 | Kirby et al. | 604/378 |
| 5,562,647 | 10/1996 | Oetjen | 604/370 |

*Primary Examiner*—Robert A. Clarke

[57] ABSTRACT

An absorbent article is provided for use in the perineal area of the body having an absorbent core having an upper body facing surface, a lower garment facing surface, first and second longitudinal sides, and first and second transverse ends. A body fluid impervious sealing wrapper, having upper and lower portions each having longitudinally and transversely extending edges along which said portions are joined, is formed around the absorbent core so as to enclose at least the entirety of the garment facing surface, the longitudinal sides and the transverse ends, thereby forming a seal. A centrally disposed opening is formed in the upper portion of the sealing wrapper thereby forming a window on the body facing surface of the absorbent core that exposes it to fluid flow. A fluid pervious layer covers at least the portion of the body facing surface on which the window is formed. The upper portion of the sealing wrapper and the pervious layer are joined so as to form a laminated layer. In another embodiment, the window is formed in a fibrous non-woven fabric that covers the longitudinal sides of the absorbent core and the window is covered by an apertured plastic film.

5 Claims, 8 Drawing Sheets

ABSORBENT ARTICLE HAVING STRIKE WINDOW

This is a division of application Ser. No. 07/767,294, filed Sep. 29, 1991 now abandoned which is hereby incorporated by reference.

FIELD OF THE INVENTION

The current invention concerns an absorbent article for use in the perineal area of the body, such as sanitary napkins, incontinence pads, and the like. More specifically, the current invention concerns an absorbent article having a strike window in its body facing surface located to receive bodily fluid, as well as a method of making such an article.

BACKGROUND OF THE INVENTION

Traditionally, absorbent articles have included a center absorbent portion having a body facing surface—that is, a surface that faces the perineum, a garment facing surface, longitudinally extending sides and transverse ends. These articles generally include an absorbent core made of loosely associated hydrophilic materials, such as wood pulp. The body facing surface of the absorbent core is covered by a layer of body fluid pervious fabric, typically referred to as a "cover". The garment facing surface and the longitudinally extending sides of the absorbent core are enclosed by a layer of body fluid impervious material, typically referred to as a "barrier", that is preferably non-wicking and pervious to gases. These layers are sometimes sealed around the absorbent core by joining them together along their longitudinal and transverse edges so as to form flanges— see, for example U.S. Pat. No. 4,678,527 (Ulman), assigned on its face to the same assignee as the current invention. In this arrangement, the cover and barrier each form a portion of the longitudinal sides of the center portion.

Alternatively, the barrier is sometimes formed into a C-shaped boat enclosing the garment facing surface and longitudinal sides of the absorbent core. In this case, the cover is wrapped around both the barrier boat and the absorbent core and the overlapping longitudinal edges of the cover are joined together—see, for example, U.S. Pat. No. 4,200,103 (Black et al.), assigned on its face to the same assignee as the current invention. This alternative method is sometimes referred to as "flow wrapping".

Unfortunately, these approaches to forming the coverings for the absorbent article suffer from several drawbacks. First, although the barrier is effective in preventing leakage through the garment facing surface and the longitudinal sides of the article, it does not prevent leakage through the transverse ends of the article, which are, at best, only partially enclosed by the barrier.

Second, more recently, the cover forming the body facing surface has been formed from an apertured plastic film. Such films give the surface of the article a feeling of dryness against the skin, as compared to the more traditional fibrous non-woven fabrics used for the cover. Although the apertured plastic film is most useful as a covering for the body facing surface that is in contact with the perineum—that is, the surface subjected directly to the fluid flow—typically, the cover also encloses the longitudinal sides of the article that bear against the user's thighs. Experience has shown that although the apertured plastic film feels dry against the skin even after having been subjected to fluid flow, contact against the user's thighs produces the hot and sticky feeling associated with plastics, rather than the more comfortable feeling associated with contact by a fibrous non-woven fabric.

Consequently, it would be desirable to provide an absorbent article that was enclosed by a body fluid impervious barrier on its transverse ends as well as its longitudinal sides. It would also be desirable to provide an absorbent article that had an apertured plastic film on its body facing surface but a fibrous non-woven fabric on it longitudinal sides where contact is made with the thighs.

SUMMARY OF THE INVENTION

It is an object of the current invention to provide an absorbent article having a body fluid impervious barrier that has a central opening for fluid passage and that seals the transverse ends of the article, as well as its longitudinal sides and garment facing surface.

It is another object of the current invention that the absorbent article have different materials covering its body facing surface and longitudinal sides, so as to provide the dry feel associated with an apertured film on its body facing surface but the comfort associated with contact by a fibrous non-woven fabric on its longitudinal sides.

These and other objects are accomplished in an absorbent article for use in the perineal area of the body having an absorbent core, a body fluid impervious sealing wrapper and a body fluid pervious layer. The absorbent core has an upper body facing surface and a lower garment facing surface, first and second longitudinal sides, and first and second transverse ends. The body fluid impervious sealing wrapper is formed around the absorbent core so as to enclose at least the entirety of the garment facing surface, the longitudinal sides and the transverse ends. However, the sealing wrapper does not cover a central portion of the body facing surface, thereby forming a window. The fluid pervious layer encloses at least the central portion of the body facing surface.

In one embodiment, the sealing wrapper comprises upper and lower portions each having longitudinally and transversely extending edges along which they are joined. The lower portion is disposed adjacent the garment facing surface and the upper portion has an opening that forms the window that is superimposed on the central portion of the body facing surface. The upper portion of the sealing wrapper and the pervious layer are joined so as to form a laminate.

In an alternate embodiment, a layer of an apertured plastic is disposed in the window and an upper sheet, which forms the window and encloses the longitudinal sides of the article that bear against the thighs, is formed from a body fluid pervious fibrous non-woven fabric.

DESCRIPTION OF THE PREFERRED EMBODIMENT

Figure 1:
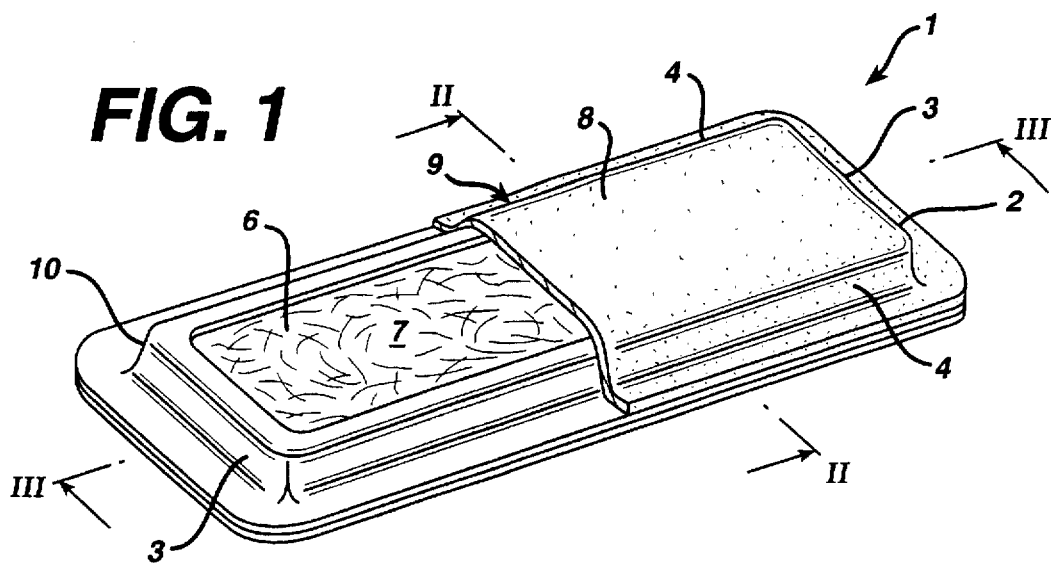
FIG. 1 is an isometric view of the absorbent article according to the current invention with a portion of the cover removed.
Figure 2:
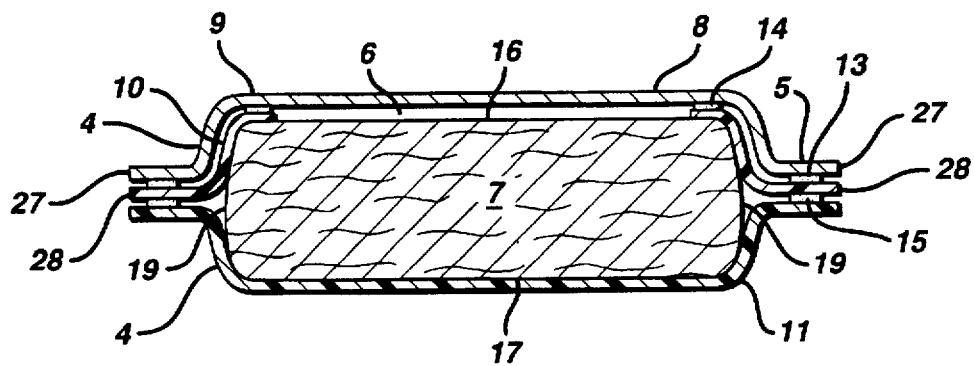
FIG. 2 is a transverse cross-section through line II—II shown in FIG. 1.
Figure 3:
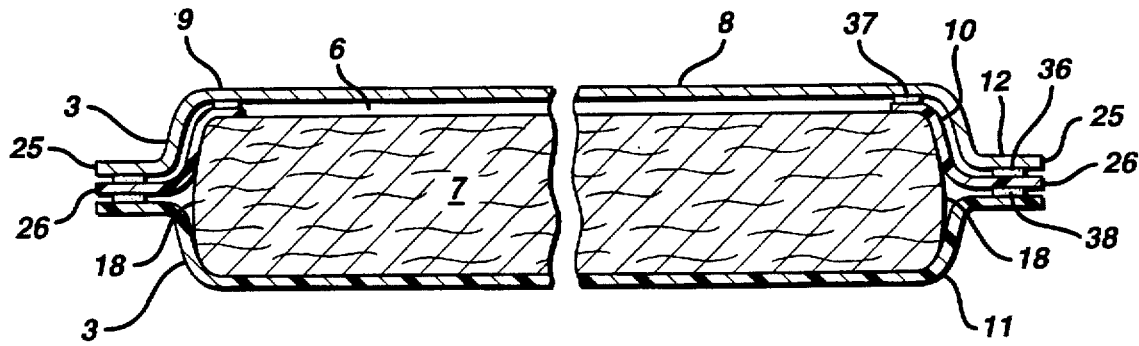
FIG. 3 is a longitudinal cross-section through the line III—III shown in FIG. 1.

There is shown in FIGS. 1-3 an embodiment of the current invention as applied to a sanitary napkin 1. The napkin is comprised of a longitudinally extending center portion 2 having right and left longitudinal sides 4 and fore and aft transverse ends 3. As explained further below, according to the current invention, the napkin 1 is enclosed in a novel way so that, unlike napkins heretofore known in the art, it is not subject to leakage through its transverse ends 3.

The center portion 2 of the napkin contains an absorbent core 7. As is known in the art, the absorbent core 7 may be comprised of a loosely associated absorbent hydrophilic material such as cellulose fibers, wood pulp, regenerated cellulose or cotton fibers, or other absorbent materials generally known in the art, including peat moss, superabsorbent materials or deodorants.

According to the current invention, the surface 16 of the absorbent core 7 that is intended to face the body of the user—specifically, the perineum—is covered by a laminated layer 9. The laminated layer 9 is formed from upper and lower sheets 8 and 10, respectively. The laminated layer 9 is preferably rectangular and has first and second longitudinally extending edges and first and second transversely extending edges.

The upper sheet 8 forms the cover for the napkin and is preferably formed from a rectangular sheet of body fluid pervious material. Such material may be any resilient, relatively non-absorbing fluid pervious material that is comfortable against the skin and capable of permitting fluid to flow to the underlying core 7 in which the fluid is retained. The upper sheet 8 should retain little or no fluid in its structure to provide a relatively dry surface next to the skin. The upper sheet 8 is preferably a fibrous non-woven fabric made of fibers or filaments of thermoplastic polymers such as polyethylene or polypropylene. Alternatively, the upper sheet 8 may be formed from an apertured polymeric film. The thickness of the cover 8 will vary from approximately 0.001 to 0.062 inch, depending on the material chosen. It should be appreciated that, for purposes of illustration, the thickness of the various layers of napkin coverings shown in the drawings, relative to the thickness of the absorbent core 7, has been exaggerated.

The lower sheet 10 may be formed from any thin, flexible, body fluid impervious material such as a polymeric film—for example, polyethylene, polypropylene or cellophane—or even a normally fluid pervious material that has been treated to be impervious, such as impregnated fluid repellent paper or non-woven fabric material. The thickness of the lower sheet 10 is typically only 0.001 to 0.002 inch. As explained further below, an opening or window 6 is centrally disposed in the lower sheet 10 and forms a window 6 on the body facing surface 16 of the absorbent core 7. In the preferred embodiment, the window 6 is smaller that the body facing surface 16 so that it exposes all but the perimeter of the body facing surface—that is, the portion of the body facing surface adjacent the longitudinal sides and transverse ends—to fluid flow.

The upper and lower sheets 8 and 10, respectively, are bonded together into a laminate by longitudinal strips 13 and 14 of adhesive applied adjacent the longitudinal edges 27 and 28 of the upper and lower sheets and adjacent the longitudinal edges of the window 6, respectively. Transverse strips 36 and 37 of adhesive are also applied adjacent the transverse edges 25 and 26 of the upper and lower sheets and adjacent the transverse edges of the window 6, respectively. The adhesive may be of the hot melt type or may be strips of double sided tape. Alternatively, the sheets may be thermally joined.

As shown in FIGS. 2 and 3, the length and width of the laminated layer 9 are sufficient to cover and extend beyond the body facing surface 16 of the napkin. Thus, in this embodiment, the laminated layer 9 forms a C-shaped configuration so that the portions of the laminated layer that are adjacent the longitudinal edges 27 and 28 form the upper portions of the longitudinal sides 4—that is, form the portions of the longitudinal sides that are adjacent the body facing surface 16, as shown in FIG. 2. In addition, as shown in FIG. 3, the portions of the laminated layer 9 that are adjacent the transverse edges 25 and 26 form the upper portions of the transverse ends 3. However, as a result of the window 6, the lower sheet 10 does not cover the central portion of the body facing surface 16 of the absorbent core 7—that is, the surface directly subjected to fluid flow. Significantly, however, the lower sheet 10 does cover the upper portions of the longitudinal sides 4 and transverse ends 3.

The napkin 1 further comprises a layer 11 of a body fluid impervious barrier disposed below the laminated layer 9. The impervious barrier 11 may comprise any of the aforementioned materials suitable for use as the lower sheet 10. As shown in FIGS. 2 and 3, the barrier 11 is formed into a C-shaped configuration and encloses the surface 17 of the absorbent core 7 intended to face the user's undergarment—specifically, the crotch of the undergarment. Like the laminated layer 9, the barrier 11 is preferably rectangular and has first and second longitudinally extending edges and first and second transversely extending edges. In addition, the length and width of the barrier 11 are sufficient to cover and extend beyond the garment facing surface 17 of the napkin so that the barrier 11 encloses the lower portions of the longitudinal sides 4 and transverse ends 3—that is, the portions that are adjacent the garment facing surface 17.

According to an important aspect of the current invention, the longitudinal and transverse edges of the laminated layer 9—more specifically, of the lower sheet 10—are joined, via strips 15 of the aforementioned adhesive, to the longitudinal and transverse edges of the barrier 11 to form longitudinally and transversely extending flanges 5 and 12, respectively. Since both the lower sheet 10 and the barrier 11 are formed from body fluid impervious materials, when joined by adhesive strips 15 they combine to form a sealing wrapper. The lower sheet 10 of the laminated layer 9 forms the upper portion of the sealing wrapper and the barrier 11 forms the lower portion of the sealing wrapper. According to the current invention, this sealing wrapper encloses the entirety of the garment facing surface, the entirety of the longitudinal sides, the entirety of the transverse ends and all but the central portion of the body facing surface of the absorbent core 7 exposed by the window 6. Thus, unlike napkins heretofore known in the art, the sealing wrapper formed by the lower sheet 10 and the barrier 11 form a body fluid impervious seal that prevents leakage through the transverse ends of the napkin 1. Accordingly, use of the laminated layer 9 according to the current invention allows a fluid pervious strike window 6 to be formed in the central portion of the body facing surface 16 while allowing a sealing barrier to be formed around the remainder of the absorbent core 7.

Although in the preferred embodiment, the window 6 and lower sheet 10 of impervious material are covered by the upper sheet 8 of pervious material, as shown in FIGS. 1–3, the invention could also be practiced by eliminating the upper sheet 8 so that the window, sides 4 and ends 3 of the napkin were not covered. Moreover, although in the preferred embodiment, the window 6 is superimposed on a central portion of the body facing surface 16, the window could also be formed eccentrically so that it exposed a portion of the body facing surface that was not centrally oriented.

Figure 4:
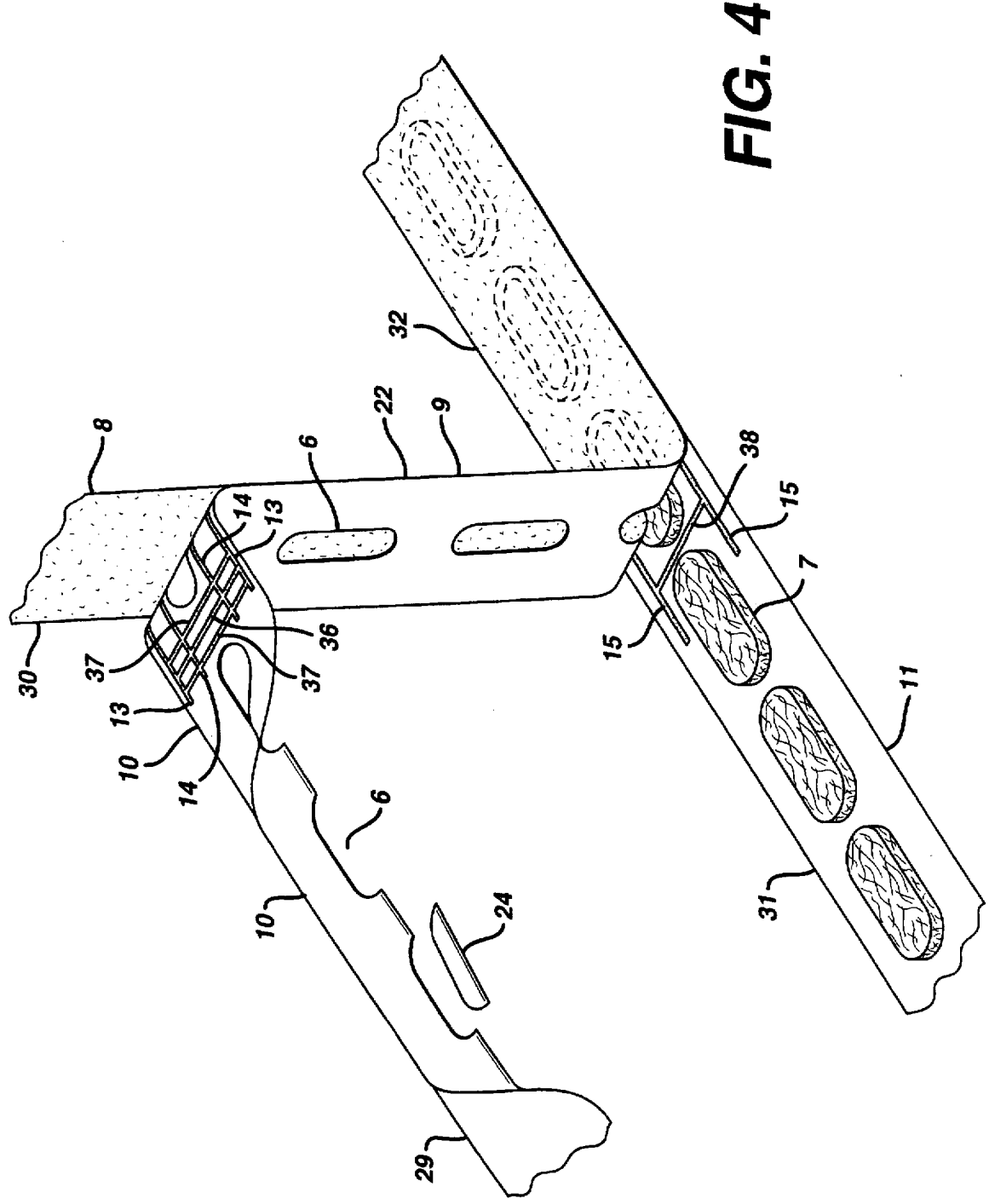
FIG. 4 is an isometric view, partially schematic, of a production line for making the article shown in FIGS. 1–3.
Figure 5A:
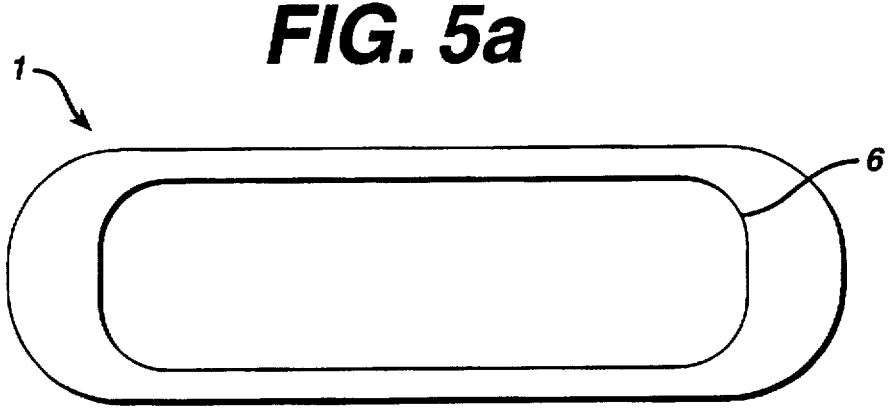
FIGS. 5(a)–(f) are plane views of alternate embodiments of the article shown in FIG. 1 showing various window shapes.
Figure 5B:
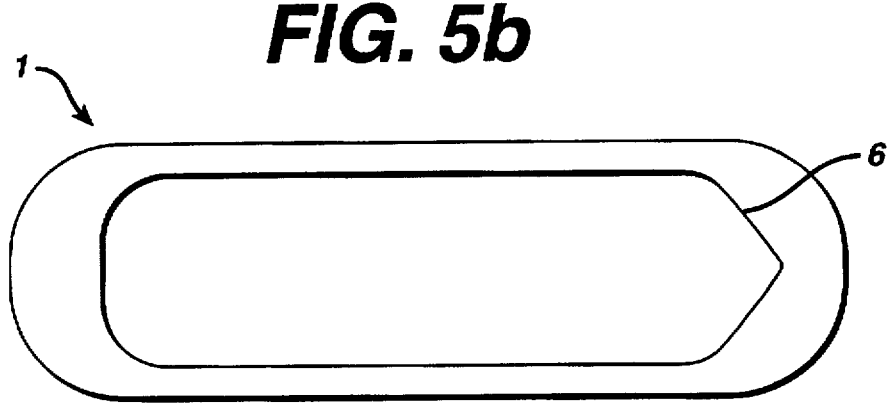
Figure 5C:
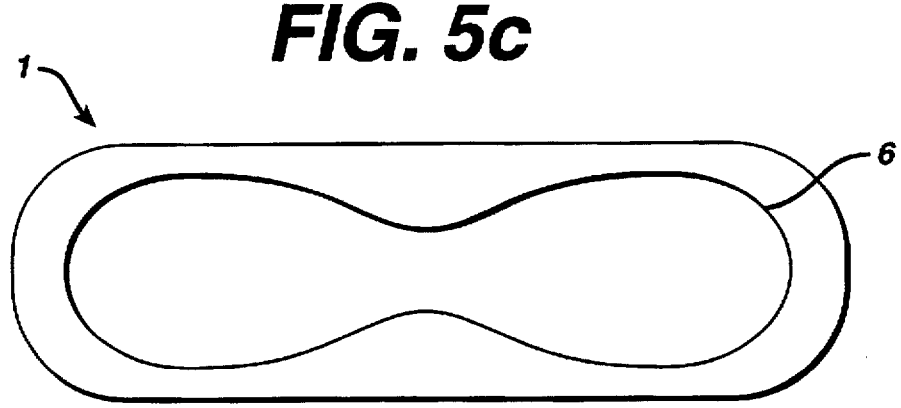
Figure 5D:
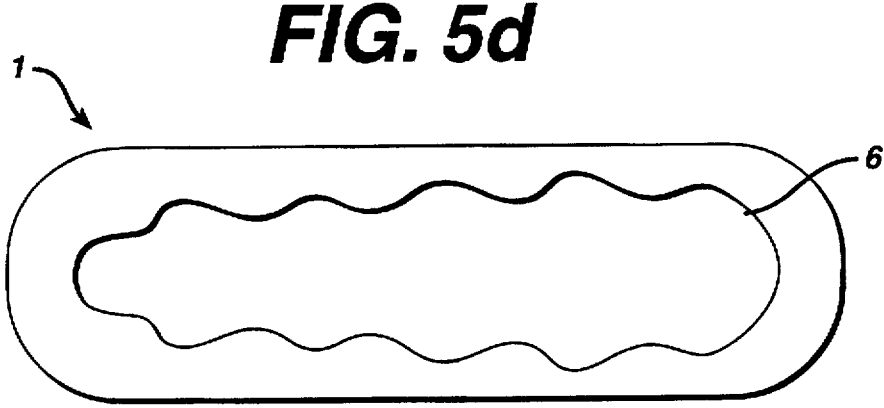
Figure 5E:
Figure 5F:

A portion of a production line for making the napkin 1 shown in FIG. 1 is shown in FIG. 4. Centrally disposed openings or "windows" 6 are formed in a strip 29 of the material that forms the lower sheet 10. In the preferred embodiment, the windows 6 are formed by using a die or water jet to cut portions 24 from the strip 29. As shown in FIG. 4, in the preferred embodiment, this cutting is facilitated by folding the strip over on itself before cutting the window 6. After the window 6 is formed, the adhesive strips 13, 14, 36 and 37 are applied to the strip 29 using conventional adhesive nozzles (not shown). The adhesive strips 13 are applied longitudinally adjacent the longitudinal edges of the strip 29. The adhesive strips 36 are applied transversely adjacent what will eventually be the transverse edges of the strip when it is cut into individual napkins. The adhesive strips 14 and 37 are applied longitudinally and transversely adjacent the longitudinal and transverse edges of the window 6.

After the adhesive has been applied, the strip 29 of lower sheet 10 material is laminated to a strip 30 of the material that forms the upper sheet or cover 8 to form a laminated strip 22. In the finished product, the laminated strip 22 forms the laminated layer 9. A strip 31 of the material that forms the barrier 11, having individual pre-cut absorbent cores 7 deposited thereon, is then passed under conventional adhesive nozzles (not shown) and adhesive strips 15 and 38 are applied longitudinally and transversely, respectively, to the strip. After application of the adhesive, the strip 31 is joined to the laminated strip 22, thereby enclosing the absorbent core 7 as shown in FIGS. 2 and 3, and forming a napkin strip 32. Subsequently, the napkin strip 32 is cut (not shown) into the individual napkins 1 shown in FIG. 1.

Alternatively, the strip 29 of lower sheet 10 material could be joined to the strip 31 of barrier 11 material first. The strip 30 of upper sheet 8 material would then subsequently be joined to the strip 29.

An important advantage of making napkins 1 according to the method described above is that it allows the windows 6 to be formed in any desired shape. FIG. 5 is illustrative of some the various window shapes that may be utilized according to the current invention.

After the absorbent core has been enclosed as explained above, wings can be attached to the napkin to protect the uer's undergarment. A preferred method of forming the wings is disclosed in co-pending U.S. patent application Ser. No. 07/766,982, (Attorney's Docket No. PPC-395), entitled "Absorbent Article With Attached Tabs and Method and Apparatus for Making Same", By Menard and Fung, hereby incorporated by reference in its entirety.

Figure 6:
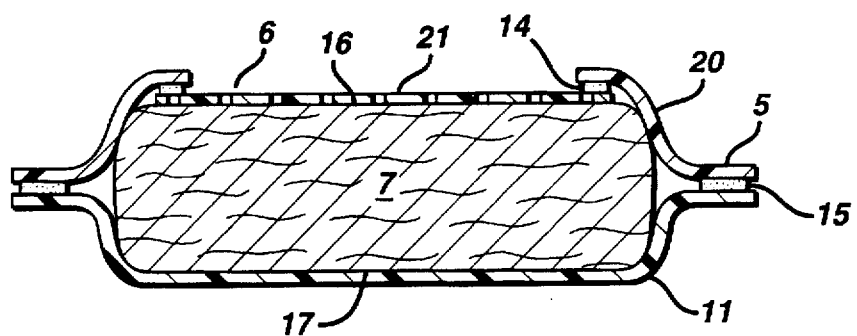
FIGS. 6 and 7 are transverse and longitudinal cross-sections, respectively, through a second embodiment of the article shown in FIGS. 1–3.
Figure 7:
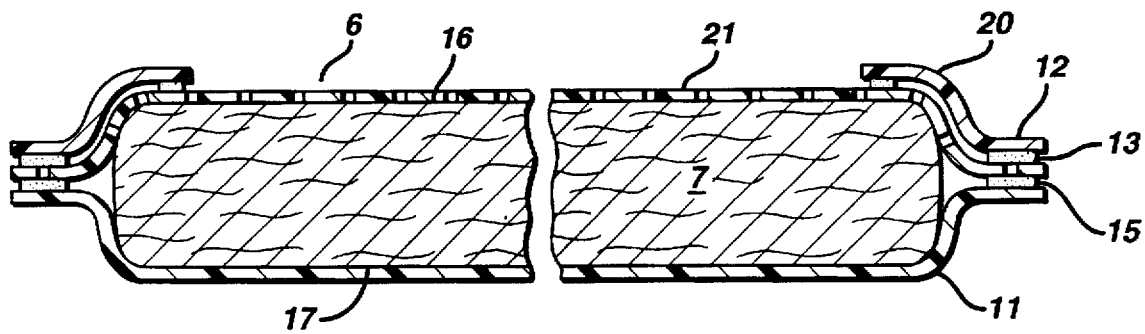

Another embodiment of the napkin shown in FIGS. 2 and 3 is shown in FIGS. 6 and 7. In this embodiment, the window 6 is formed in an upper sheet 20 of body fluid pervious material. The upper sheet 20 is laminated, via adhesive strips 13 and 14, to a lower sheet 21 that is also formed from a body fluid pervious material. As shown in FIG. 6, in this embodiment the width of the lower sheet 21 may be narrower than that of the upper sheet 20 so that only the upper sheet encloses the longitudinal sides of the absorbent core 7.

The laminated layer is then joined, via adhesive strips 15 applied adjacent the longitudinal and transverse edges of the laminated layer, to the barrier 11, thereby enclosing the absorbent core 7 and forming longitudinally and transversely extending flanges 5 and 12, respectively.

The embodiment shown in FIGS. 6 and 7 is most advantageously used by forming the lower sheet 21 from an apertured plastic film, such as Reticulon™, available from Chicopee Mills, Inc. of New York, N.Y., a division of Johnson & Johnson Corporation. As previously discussed, such films have the advantage of feeling dry against the skin even though subjected to fluid flow, making them well suited for use against the perineum. However, they are uncomfortable when pressed against the user's thighs, as occurs if they are used as a covering for the longitudinal sides of the napkin. Accordingly, the embodiment shown in FIGS. 6 and 7 provides the best of both worlds. An apertured plastic film 21 is used within the strike window 6 that is applied to the perineum and subjected to direct fluid flow, and a fibrous non-woven material, disposed outwardly from the apertured plastic film, is used for the upper sheet 20 that forms the longitudinal sides of the napkin that press against the user's thighs.

Although in the embodiments shown in FIGS. 6 and 7, the sheet 21 of apertured plastic film is shown as being below the sheet 20 of fibrous non-woven material, the invention could also be practiced by attaching the sheet 21 of apertured plastic film above the sheet 20 of fibrous non-woven material provided the non-woven material still formed at least the upper portion of the sides of the napkin—that is, provided the non-woven material was still at least laterally outwardly disposed from the apertured plastic film—so that the non-woven material and not the apertured plastic film pressed against the user's thighs.

Figure 8:
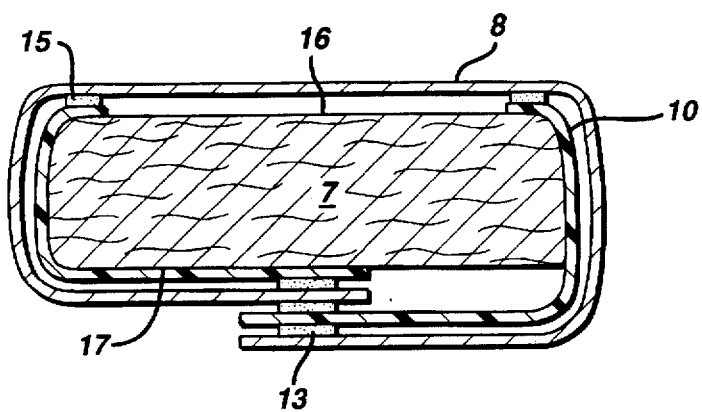
FIGS. 8 and 9 are transverse and longitudinal cross-sections, respectively, through a third embodiment of the article shown in FIGS. 1–3.
Figure 9:
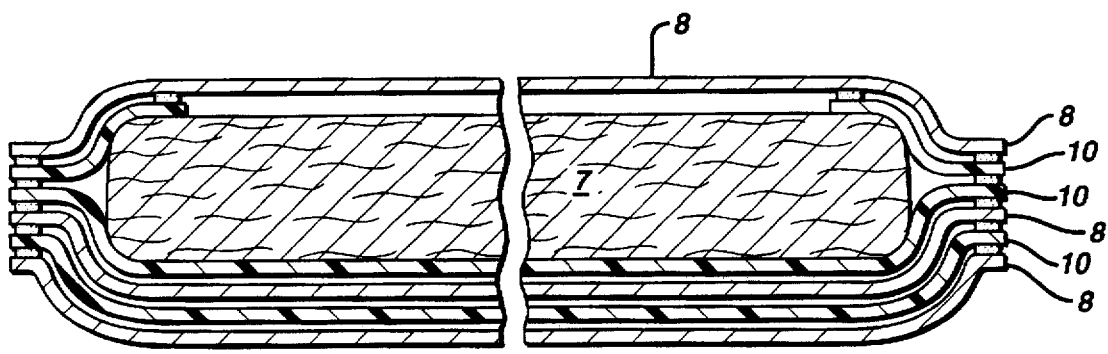

Another embodiment of the current invention is shown in FIGS. 8 and 9. This embodiment is functionally similar to that shown in FIGS. 2 and 3 in that a fluid impervious wrapper is formed around the transverse ends, as well as the garment facing surface and longitudinal sides of the absorbent core. However, rather than joining the layers so as to form longitudinal flanges, the napkin is enclosed by the aforementioned "flow wrapping" method. Flow wrapping has the advantage that the sides of the napkin that bear against the user's thighs are soft and smooth since there are no edges or joints in these areas.

Figure 10:
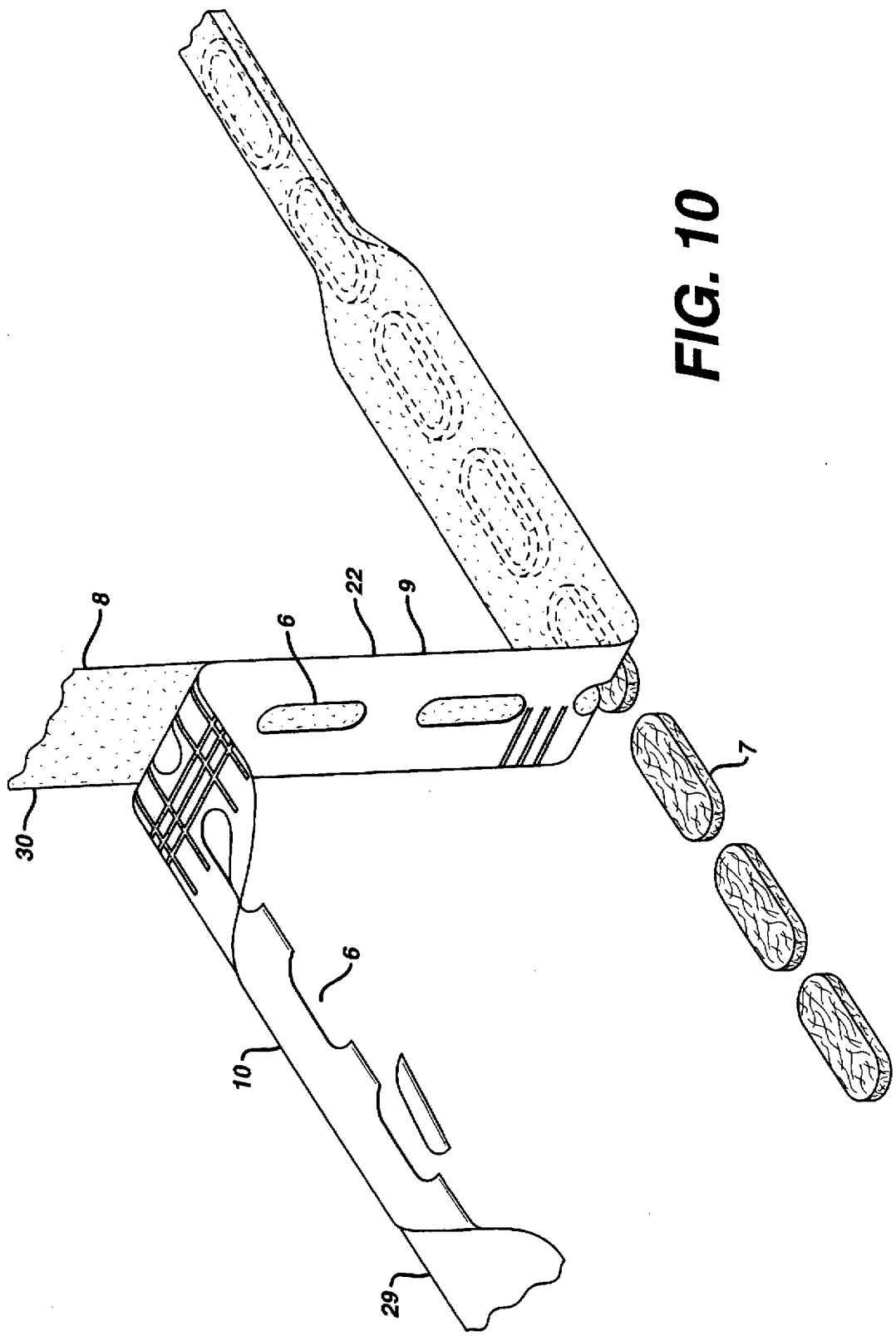
FIG. 10 is an isometric view, partially schematic, of an alternate embodiment of the production line shown in FIG. 4 for making the article shown in FIGS. 8 and 9.

According to the flow wrapping method, as shown in FIG. 10, the strip 29 of the lower sheet 10 material is laminated to the strip 30 of upper sheet 8 material to form a laminated strip 22, as before. However, the width of the laminated strip is more than twice the combined width and thickness of the absorbent core 7. Thus, the laminated strip 22 can be wrapped around the cores 7 so as to form a tube. The opposing longitudinal edges of the strip 22 are joined together along overlapping portions disposed adjacent the garment facing surface 17, as shown in FIG. 8. Next, the upper and lower portions of the transverse edges of the tube are joined together, as shown in FIG. 9, to form what will become transversely extending flanges in the finished product, thereby completely enclosing the absorbent cores 7. Subsequently, the tube is cut into individual napkins.

It should be noted that, according to this embodiment, the lower sheet 10 alone forms the sealing wrapper. There is no need for a separate barrier 11 to form the lower portion of the wrapper.

Figure 11:
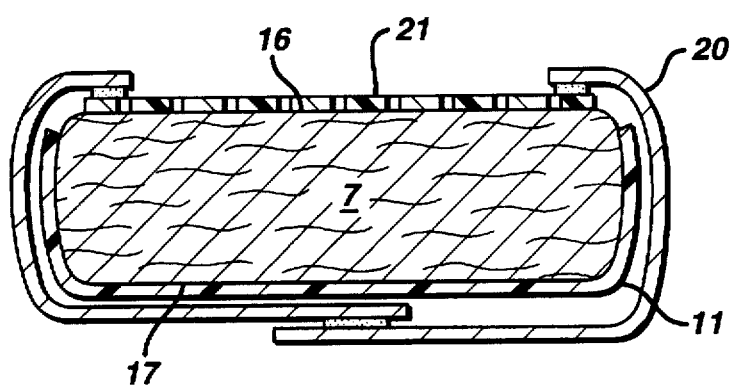
FIG. 11 is a transverse cross-section through another embodiment of the article shown in FIGS. 6 and 7.

FIG. 11 shows another embodiment of the napkin according to the current invention using the flow wrapping method. This embodiment is functionally similar to the embodiment shown in FIGS. 6 and 7 in that preferably a lower sheet 21 of apertured plastic film is used to cover a window 6 formed in a fibrous non-woven fabric upper sheet 20 adapted to form the longitudinal sides, so that the advantages of both of these materials are optimally realized. However, in this embodiment, the laminated layer formed by joining the upper and lower sheets 20 and 21 is wrapped around an absorbent core 7 after the core has been enclosed on its garment facing surface 17 and longitudinal sides by a barrier 11.

As the foregoing indicates, the current invention affords great flexibility in the design of sanitary napkins, allowing the use of a wide range of covering materials and allowing these materials to be attached to the napkin in various ways to achieve an optimum configuration. Although the invention has been illustrated as applied to an approximately rectangular napkin, the invention is equally applicable to an oval or similarly shaped napkin in which the boundary between the longitudinal sides and the transverse ends is not clearly defined. Moreover, although the invention has been explained with reference to a sanitary napkin, the invention is also suitable for use in other-absorbent articles, such as incontinence pads the like. As the various embodiments disclosed above indicate, the present invention may be embodied in many specific forms without departing from the spirit or essential attributes thereof and, accordingly, reference should be made to the appended claims, rather than to the foregoing specification, as indicating the scope of the invention.

What is claimed is:

1. An absorbent article for use in conjunction with a body having a perineal area comprising:

a) an absorbent core having (i) an upper body facing surface and a lower garment facing surface, (ii) first and second longitudinal sides, (iii) first and second transverse ends, and (iv) a perimeter;

b) a body side wrapper superposed on said absorbent core comprising a body fluid impervious sealing wrapper which extends about said perimeter of said absorbent core including upper portions of (i) said longitudinal sides and (ii) said transverse ends, said sealing wrapper not covering a substantially centrally located portion of said body facing surface, thereby forming an opening, and a body fluid pervious material enclosing at least said body facing surface not covered by said sealing wrapper; and c) a garment side wrapper comprising a second body fluid impervious sealing wrapper which extends about said perimeter of said absorbent core including lower portions of (i) said longitudinal sides, (ii) said transverse ends, and (iii) said garment facing surface; wherein portions of said upper and lower wrappers adjacent said absorbent core perimeter are joined to form longitudinally and transversely extending flanges and said upper potion of said sealing wrapper and the pervious layer are joined to form a laminate; a portion of laminate adjacent to said first longitudinal edge overlaps and is joined to a second portion of said laminate adjacent second longitudinal edge, thereby forming a tube with sealed ends enclosing the absorbent core.

2. The absorbent article according to claim 1, wherein said pervious layer is disposed outward from said upper portion of said upper sealing wrapper, whereby said pervious layer is adapted to contact said perineal area of said body in use.

3. The absorbent article according to claim 1, wherein a portion of said upper portion of said sealing wrapper adjacent said opening encloses portions of said body facing surface adjacent said longitudinal sides and adjacent said transverse ends of said absorbent core.

4. The absorbent article according to claim 1, wherein said pervious layer has longitudinally and transversely extending edges, said pervious layer being joined along portions adjacent its edges to said flanges.

5. The absorbent article according to claim 1, wherein said first and second transverse edges of said laminate form first and second ends of said tube, each tube end having upper and lower edges joined together to form a transversely extending flange.

* * * * *